United States Patent
Wawro

(10) Patent No.: US 11,806,138 B2
(45) Date of Patent: Nov. 7, 2023

(54) PATIENT PHOTOSENSOR

(71) Applicant: Welch Allyn, Inc., Skaneateles Falls, NY (US)

(72) Inventor: Thaddeus J. Wawro, Skaneateles Falls, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 464 days.

(21) Appl. No.: 17/030,716

(22) Filed: Sep. 24, 2020

(65) Prior Publication Data

US 2021/0093238 A1 Apr. 1, 2021

Related U.S. Application Data

(60) Provisional application No. 62/906,927, filed on Sep. 27, 2019.

(51) Int. Cl.
*A61B 5/1455* (2006.01)
*A61B 5/00* (2006.01)

(52) U.S. Cl.
CPC ........ *A61B 5/14552* (2013.01); *A61B 5/6823* (2013.01); *A61B 5/6831* (2013.01); *A61B 5/6832* (2013.01)

(58) Field of Classification Search
CPC .............. A61B 5/1455; A61B 5/02416; A61B 5/14552; A61B 5/6832
See application file for complete search history.

(56) References Cited

U.S. PATENT DOCUMENTS

| | | | |
|---|---|---|---|
| 7,643,860 B2 * | 1/2010 | Gueissaz | ............ A61B 5/02416 600/344 |
| 8,554,297 B2 | 10/2013 | Moon et al. | |
| 2016/0067499 A1 | 3/2016 | Owen et al. | |

* cited by examiner

*Primary Examiner* — Marjan Fardanesh
(74) *Attorney, Agent, or Firm* — Barnes & Thornburg LLP

(57) ABSTRACT

Devices, systems, and methods for patient sensing include a patient sensor having a light diffuser arranged to provide a light field in which photoelectric sensors can be positioned to provide enhanced detection of physiological parameters of the patient. The light diffuser is connected with a sensor baffle to assist in avoiding interference.

20 Claims, 5 Drawing Sheets

PATIENT PHOTOSENSOR

CROSS-REFERENCE TO RELATED APPLICATIONS

This U.S. Non-provisional Patent Application claims the benefit of priority to U.S. Provisional Application No. 62/906,927, filed on Sep. 27, 2019, entitled Patient Photosensor, the contents of which are incorporated by reference in their entirety, including but without limitation at least those portions relating to patient sensors.

BACKGROUND

The present disclosure relates to devices, systems, and methods for sensors. More specifically, the present disclosure relates to devices, systems, and methods for sensors for monitoring patients.

Patient monitoring, for example, via patient sensors, can present interesting challenges to determining physiological parameters. Patient sensors which use light, such as by photosensors measuring light chrematistics can provide reliable results through non-invasive techniques. Yet, such patient photosensors can be susceptible to external factors such as interfering light sources, and/or undesirable positioning on the patient's body. Such external factors can reduce the reliability of information received from patient sensors.

SUMMARY

The present application discloses one or more of the features recited in the appended claims and/or the following features which, alone or in any combination, may comprise patentable subject matter.

According to an aspect of the present disclosure, a patient sensor may include a sensor baffle including a diffuser platform having at least one light opening defined therethrough and at least one canister extending from the diffuser platform to define a light pathway, at least one photodetector arranged to receive light through the light pathway of the at least one canister; and a light diffuser configured for mounting to the sensor baffle. The light diffuser may include a diffuser body and a diffuser arm extending from the body for extension through the at least one light opening to receive light from a light source for diffusion through the diffuser body.

In some embodiments, the diffuser body may include at least one opening arranged to correspond with the at least one canister. The at least one opening may be configured to receive the at least one canister therethrough. The diffuser body may be configured to disperse light received via the diffuser arm circumferentially about the extension of at least one canister. The at least one canister may extend through the diffuser body to receive light reflected from a patient's body. The at least one canister may extend through and at least partly beyond the diffuser body to receive light reflected from a patient's body.

In some embodiments, the diffuser platform may include a first side and the at least one light opening extends between the first side and a second side opposite the first side. The diffuser arm may be configured to extend though the light opening to communicate with the light source on the second side of the diffuser platform to receive light for diffusion through the diffuser body. The diffuser arm may be flared in shape having decreasing width proceeding away from the diffuser body. The diffuser arm may include a source end formed opposite to the diffuser body that is configured to engage with a light source to receive light for communication through the body.

In some embodiments, the sensor baffle may include a contact end configured for engagement with a patient's body to allow detection of physiological parameters. The sensor baffle may include a rim extending from the diffuser platform towards the contact end. The rim and the diffuser platform may define a diffuser receptacle for receiving the light diffuser. In some embodiments, the diffuser receptacle may include an open top for providing diffused light to a patient's body. The at least one canister may extend through the diffuser receptacle to receive light reflected from the patient's body through the light pathway.

In some embodiments, the light pathway of the at least one canister may be defined by a tapered inner surface of the at least one canister. The diffuser body may include a backside surface angled away from the diffuser arm. In some embodiments, the backside surface of the diffuser body may include texture for directing light through the diffuser body. The texture may be arranged annularly about the diffuser arm. The texture may be formed with gradient proceeding away from the diffuser arm.

In some embodiments, the diffuser body may include a frontside surface sloped towards an interior of the diffuser body. The frontside surface may be formed to define a depression. The frontside surface may be formed to have a negative cone shape. The negative cone shape may be tapered.

According to another aspect of the present disclosure, a method of assembly of a patient sensor may include forming a sensor baffle, and applying a light diffuser to the sensor baffle. In some embodiments, applying the diffuser may include injection molding the diffuser to the sensor baffle.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION

Figure 1:
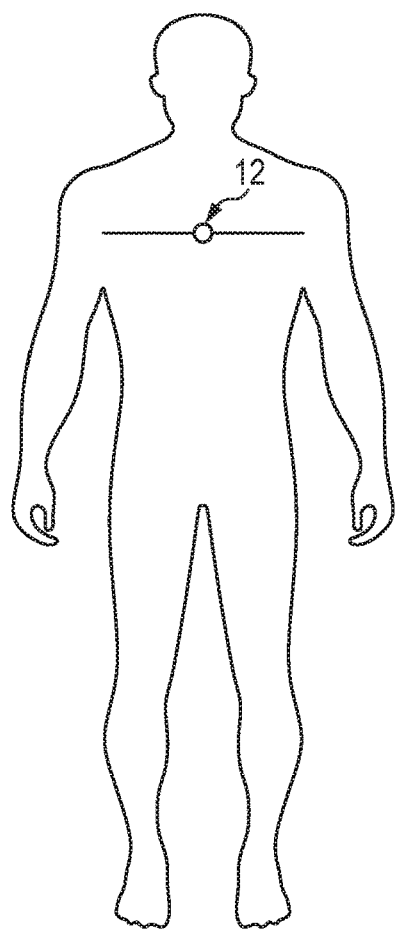
FIG. 1 is an elevation view of a patient having a patient sensor secured to the patient's body at the chest area.

For the purposes of promoting an understanding of the principles of the disclosure, reference will now be made to a number of illustrative embodiments illustrated in the drawings and specific language will be used to describe the same.

Light-based patient sensors can enable detection of patient conditions based on observations from light such as infrared light. Considering the status and/or changes to light that has been directed to the patient's body can be used to determine physiological parameters of the patient with relative accuracy and/or precision. For example, a patient's blood oxygen saturation, such as personal peripheral capillary oxygen saturation levels ($SpO_2$) as a measure of oxygen-carrying hemoglobin relative to the amount of hemoglobin not carrying oxygen in the patient's blood, can be determined based on observation of infrared light provided into the patient's skin.

Traditional $SpO_2$ sensors such as pulse oximeters may receive light that has engaged the patient's body, either reflected by and/or transmitted through the patient's body. The light is directed into the patient's skin where some of the light can be absorbed by the blood vessels. Light received after engagement with the patient's body can be analyzed to determine the changing absorbance of light, for example, during the patient's pulse rhythm. By measuring changes in two different wavelengths of light, the absorbance due to the pulsing arterial blood alone can be determined, excluding other sources of light absorption such as from venous blood, skin, bone, muscle, and/or fat. Thus, observing the light after engagement with the patient allows determination of the patient's blood oxygenation levels based on the characteristics of light received.

By more specific example, a photoplethysmogram (PPG) sensor can be applied as a pulse oximeter for providing an optically-obtained plethysmogram indicating the change in volume of blood at specific site within the patient's tissue. However, such sensors can be challenging to implement. Properly engaging the light with the patient's body and/or properly receiving light after engagement can be challenging, and/or can require precision arrangement and/or orientation of the sensor on the patient's body which can burden the caregiver and/or patient.

Referring now to FIG. 1, a patient sensor 12 is shown applied to a patient's body. As discussed in additional detail herein, the patient sensor 12 is embodied as a PPG sensor for receiving light reflected from the patient for determining physiological parameters. In the illustrative embodiment, the patient sensor 12 is applied to the patient chest, secured in place by a chest strap, although in some embodiments, may be secured using adhesive or other suitable manner of retention.

Figure 2:
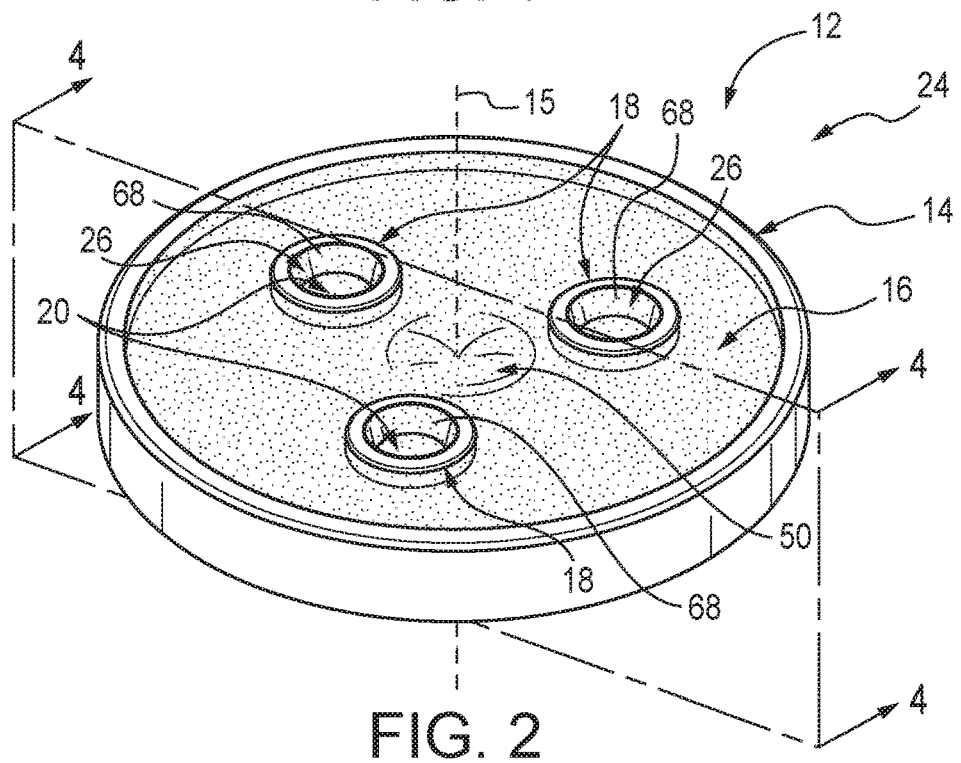
FIG. 2 is a perspective view of the patient sensor of FIG. 1 showing that the patient sensor includes a baffle and a light diffuser for diffusing light for communication to the patient's skin such that light reflected back to photodetectors of the patient sensor can be used to determine one or more physiological parameters of the patient.

Referring to FIG. 2, the patient sensor 12 is shown having a contact end 24, exposed for descriptive ease, which can be engaged with the patient's skin. The patient sensor 12 includes a baffle 14 and a light diffuser 16 for illumination to provide diffused light to the patient's body. The light diffuser 16 is illustratively embodied as a translucent body, formed with circular shape, for diffusing light to be provided to the patient's skin.

The patient sensor 12 includes canisters 18 projecting through light diffuser 16 to receive light reflected from the patient's body. Photoelectric detectors 20 are each arranged within respective canisters 18 to receive light reflected from the patient for determining patient physiological characteristics. As discussed in additional detail herein, the light diffuser 16 is arranged to provide a light field which envelops the canisters 18, and thus the photoelectric detectors 20, to provide enhanced distribution of light to the patient's body, while avoiding interference from less desirable light.

Figure 3:
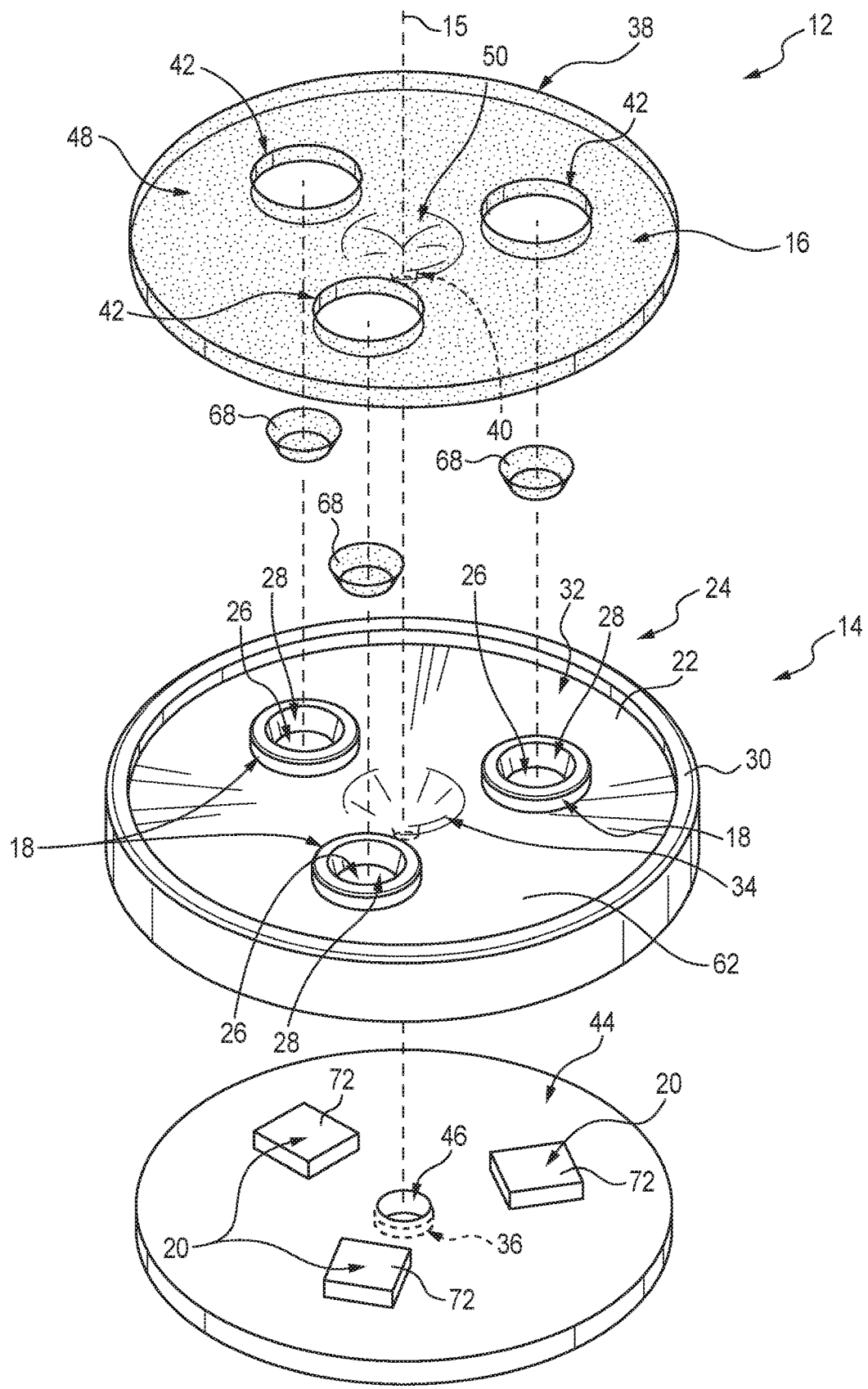
FIG. 3 is an exploded perspective view of the patient sensor of FIGS. 1 and 2 showing that the baffle includes a diffuser platform and canisters projecting from the diffuser platform to define light pathways for receiving reflected light from the patient's body, and photoelectric sensors arranged beneath the diffuser platform for receiving light through the light pathways.

Referring now to FIG. 3, the baffle 14 illustratively includes a platform 22. Each canister 18 extends from the platform 22 towards the contact end 24 of the baffle 14. Each canister 18 is illustratively formed to have circular shape, but in some embodiments, may take any other suitable shape. The canisters 18 each define a light pathway 26 therethrough for receiving light from the patient's body for communication to the photoelectric detectors 20. The canisters 18 each extend through the light diffuser 16 to receive light through their open end 28 for reception by the photoelectric detectors 20. The projection of the canisters 18 through the light diffuser 16 can avoid interference from light provided by the light diffuser 16 that has not yet engaged the patient's body being received by the photoelectric detectors 20.

The baffle 14 includes a rim 30 extending from the platform 22 towards the contact end 24. The rim 30 and the platform 22 collectively define a diffuser receptacle 32 having an open top for receiving the light diffuser 16 therein. The diffuser receptacle 32 is illustratively shaped to correspond with the light diffuser 16. Light communicated through the light diffuser 16 through the open top of the diffuser receptacle 32 can be directed to the patient's body by engaging the contact end 24 of the baffle 14 with the patient.

Figure 4:
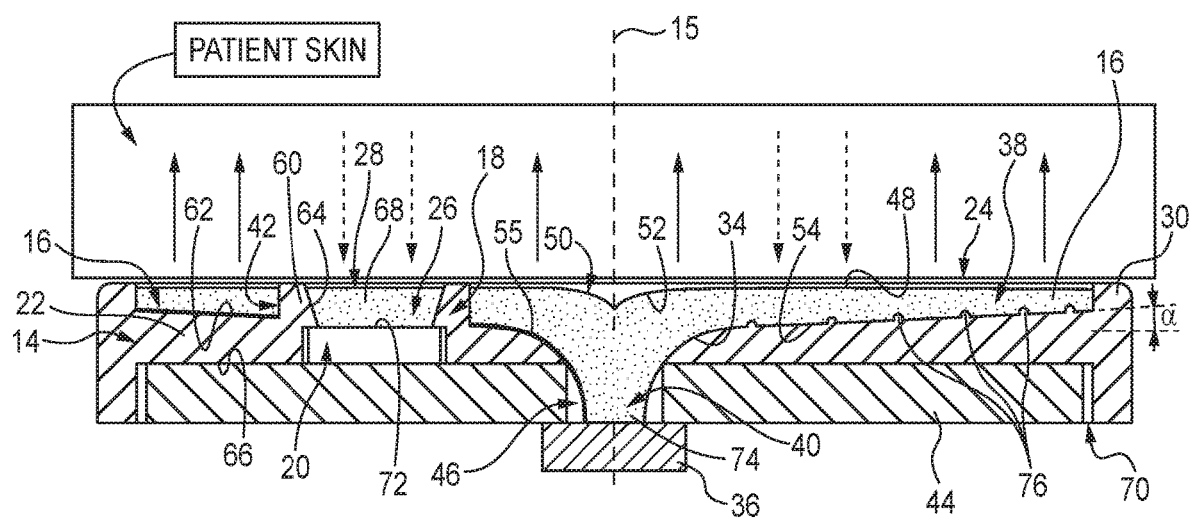
FIG. 4 is a cross-sectional view of the patient sensor of FIGS. 1-3 taken along the plane 4-4 in FIG. 2 showing the patient sensor having a contact end applied to the patient's skin and showing that the diffuser includes a diffuser body and a diffuser arm for communication with a light source.

In the illustrative embodiment, the canisters 18 and rim 30 each project from the diffuser platform 22 towards the contact end 24 to the same extent to terminate in the same plane. The similar extension of the canisters 18 and rim 30 can permit engagement of each of the canisters 18 and rim 30 with the patient's skin, as depicted in FIG. 4, to avoid intrusion of external light into the light field defined by the area of projection of diffused light provided by the diffuser 16 and to avoid cross-communication of light from the diffuser 16 directly into the photoelectric detectors 20 without engagement within the patient's body. Accordingly, the canisters 18, and thus the photoelectric detectors 20, can be arranged within the area of the light field without interference by cross-communication.

Referring still to FIG. 3, the platform 22 of the sensor baffle 24 includes a light opening 34 defined therein for communicating light from a light source 36. The light opening 34 is illustratively arranged centered between the canisters 18 to allow even distribution of light about the photoelectric detectors 20 via the light diffuser 16. The canisters 18 are illustratively embodied to include three canisters 18 arranged equidistant from the central axis 15. The canisters 18 are evenly spaced apart from each other in the circumferential direction about the axis 15. In some embodiments, the canisters 18 may include any suitable number and/or arrangement to receive light reflected from the patient's body.

As previously mentioned, the light diffuser 16 is embodied as a semi-transparent or translucent element including a diffuser body 38 and a diffuser arm 40 extending from the diffuser body 38. The diffuser body 38 is illustratively formed complimentary to the diffuser receptacle 32 such that the diffuser body 38 is received within the receptacle 32 and the diffuser arm 40 extends through the light opening 34. The diffuser body 38 includes a number of openings 42 each penetrating therethrough and arranged for receiving a corresponding one of the canisters 18 extending through the diffuser body 38.

The photoelectric detectors 20 are illustratively arranged to correspond with the position of the canisters 18. The photoelectric detectors 20 are each positioned within the light pathway 26 of a corresponding canister 18 to receive light reflected from the patient's body through the canister 18. The photoelectric detectors 20 are embodied to be mounted on a control board 44 received by the baffle 14 opposite the contact end 24.

A light source 36, embodied as an LED, is mounted with the control board 44 for engaging with the diffuser arm 40 to provide light for diffusion through the light diffuser 16. The light source 36 is illustratively mounted to a lower side of the control board 44. The control board 44 includes an opening 46 formed therethrough having the light source 36 arranged in corresponding position for communicating light through the opening 46 to the light diffuser 16.

Referring now to FIG. 4, the cross-sectional profile of the light diffuser 16 can be observed. The light diffuser 16 includes a surface 48 (upper surface in the orientation of FIG. 4) arranged facing towards the contact end 24 of the baffle 14. The light diffuser 16 includes a light director 50 embodied as a depression defined by sloped sections 52 of the surface 48.

The light director 50 is illustratively formed centrally about the axis 15 having a tapered negative conical shape. The light director 50 can assist in distributing light from the light source 36, internally within the diffuser 16, laterally towards the perimeter of the diffuser body 38 to enhance the distribution of light about the light diffuser 16.

The light diffuser 16 includes a surface 54 (lower surface in the orientation of FIG. 4) formed collectively by portions of the diffuser body 38 and diffuser arm 40. The surface 54 along the extent of the diffuser body 38 defines a slope α from horizontal, facing away from the diffuser arm 40. The slope α may be defined within the range of about 0.1 to about 5 degrees from horizontal in the orientation of FIG. 4. Although illustratively embodied as a constant slope α along the diffuser body 38, the surface 54 may include curvature in some embodiments.

The diffuser arm 40 illustratively extends from the diffuser body 38 to define a flared shape having decreasing width proceeding away from the diffuser body 38. The surface 54 along the extent of the diffuser arm 40 is shaped according to the flared shape of the diffuser arm 40. In some embodiments, a reflective layer 55 may be arranged on the surface 54 between the diffuser 16 and the baffle 14 to direct light back into the diffuser 16.

Still referring to FIG. 4, each canister 18 extends through the opening 42 of the diffuser 16 towards the contact end 24 of the baffle 14. The canister 18 includes a canister wall 60 extending from an upper side 62 of the platform 22, and having an interior surface 64 that defines the light pathway 26. The light pathway 26 is thus defined through the surfaces 48, 54 of the diffuser 16 to block against interference from the diffused light provided from the diffuser 16. Each light pathway 26 penetrates through an upper side 62 of the platform 22 and through a lower side 66 of the platform 22 opposite the upper side 62.

The interior surface 64 of each canister 18 is illustratively sloped to face upwards (in the orientation of FIG. 4) to form the light pathway 26 with taper to focus light received toward the center of the light pathway 26. The light pathways 26 each include a complimentary filler 68 received therein to protect the photoelectric detectors 20 from contamination. The fillers 68 may be formed of transparent and/or translucent material, and in some embodiments may include the same materials as the diffuser 16.

In the illustrative embodiment of FIG. 4, the photoelectric detectors 20 are each positioned at an end of the light pathway 26 opposite the contact end 24. The photoelectric detectors 20 are illustratively embedded into the platform 22. The photoelectric detectors 20 are illustratively arranged such that their photoreceptor surface 72 is arranged approximately even with the upper side 62 of the platform 22 (in the vertical direction in the orientation of FIG. 4). However, in some embodiments, the photoelectric detectors 20 may be arranged with any suitable positioning, for example, the photoelectric detectors 20 may be arranged close to the contact end 24 of the baffle 14, and/or such that their photoreceptor surfaces 72 are positioned within the diffuser body 38 (vertically within the surfaces 48, 54 in the orientation of FIG. 4).

The diffuser arm 40 is arranged in communication with the light source 36 to receive light for communication through the diffuser body 38. The diffuser arm 40 includes a source end 74 formed opposite to the diffuser body 38 for engagement with the light source 36. In the illustrative embodiment, the source end 74 is engaged with the light source 36 by contact therewith, but in some embodiments, the source end 74 may be arranged closely spaced-apart from the light source 36.

Figure 5A:
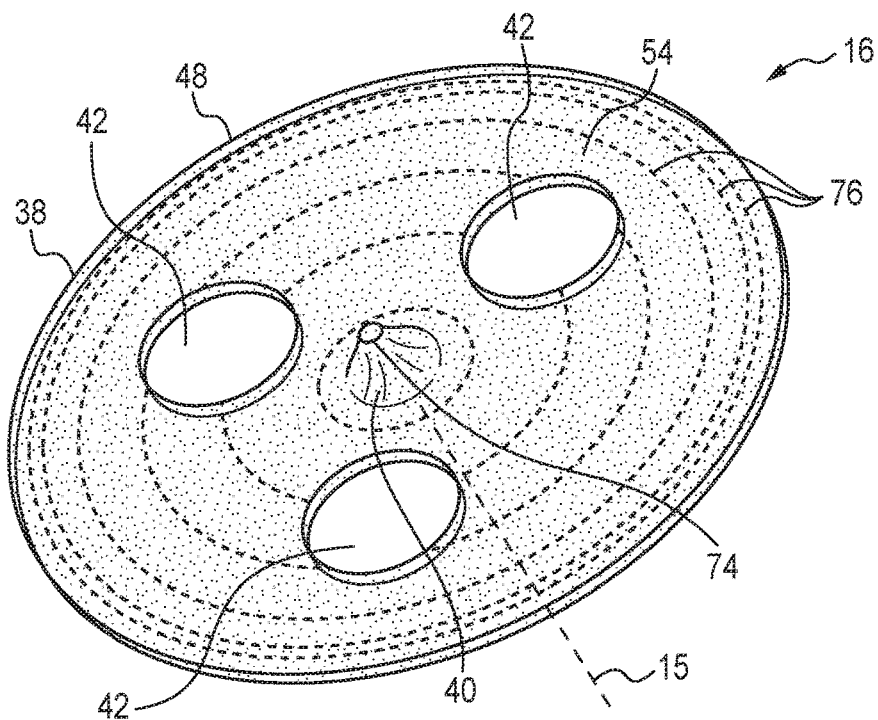
FIG. 5A is lower perspective view of the diffuser of the patient sensor of FIGS. 1-4 showing that an underside of the diffuser include a texture.
Figure 5B:
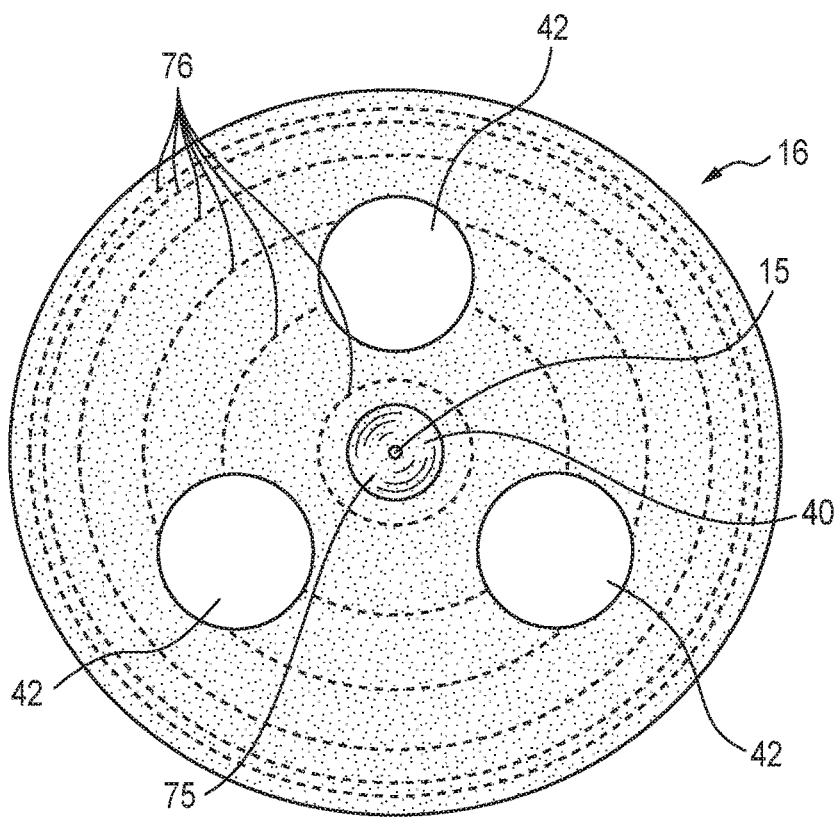
FIG. 5B is bottom plan view of the diffuser of FIG. 5A showing that the texture is arranged with a gradient proceeding away from the diffuser arm.

Referring now to FIGS. 5A and 5B, the light diffuser 16 is shown in isolation for descriptive ease. The (lower) surface 54 illustratively includes texture 76 embodied as etchings, shown in broken line, forming a light-guide plate for directing light upwards towards the upper surface 48. Referring briefly to FIG. 4, the texture 76 is illustratively formed as a number of dome-shaped etches formed annularly about the axis 15 and/or the diffuser arm 40. The texture 76 is illustratively formed with a gradient such that the spacing between adjacent annular etches decreases proceeding away from the diffuser arm 40. In some embodiments, any suitable manner of texture may be included on the lower surface 54 to encourage evenly distributed light towards the upper surface 48, for example but without limitation, the texture may be formed by printed dot pattern with continuous distribution across some or all of the surface 54. Such printed dot pattern may include gradient proceeding away from the diffuser arm 40 as progressive arrangement in the spacing between printed dots, and/or progressive arrangement of size and/or shape of printed dots.

Figure 6:
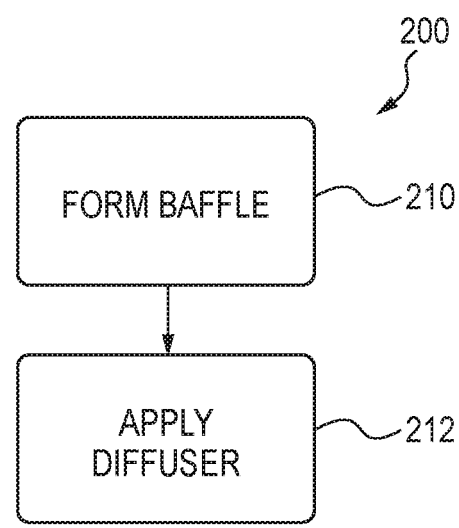
FIG. 6 is a flow diagram indicating a manner of assembly of the patient sensor of FIGS. 1-5B.

Referring now to FIG. 6, an illustrative manner of assembly of the patient sensor 12 is indicated by numeral 200. In the illustrative embodiment, the baffle 14 is formed in box 210. The baffle 14 is illustratively formed by injection molding, although in some embodiments, may include by any suitable manner of formation, for example but without limitation, casting, additive forming, vacuum forming, milling, among others.

In box 212, the diffuser 16 is applied. In the illustrative embodiment, the diffuser 16 is applied by injection molding, as an additional shot of a multi-injection molding operation. In some embodiments, the diffuser 16 may be applied as an insert molding of the injection molding of the baffle 14, or the baffle 14 may be formed as an insert molding of the injection molding of the diffuser 16. In some embodiments, the diffuser 16 may be partly or wholly formed apart from the baffle 14 and may be applied by engaging the diffuser 16 with the baffle 14, for example, by setting the diffuser 16 in place within the diffuser receptacle 32.

Figure 7:
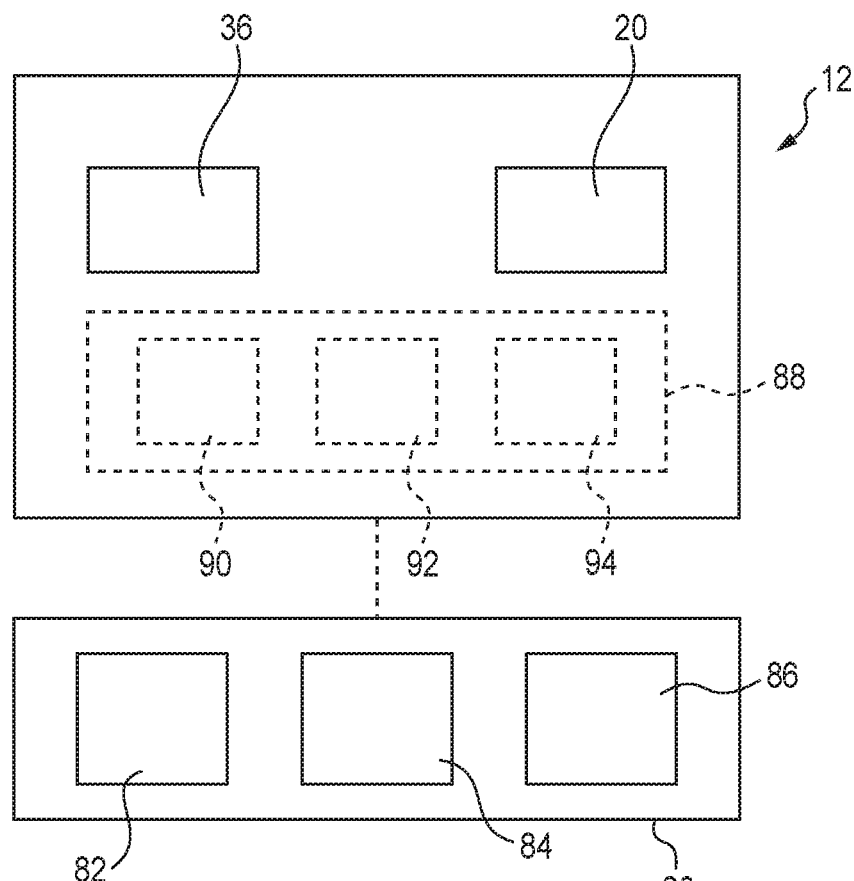
FIG. 7 is diagrammatic view of the patient sensor of FIGS. 1-4 arranged in communication with a control system to govern operation of the light source and photodetectors.

As shown in FIG. 7, the patient sensor 12 is arranged in connection with a control system 80. The control system 80 illustratively includes a processor 82 embodied as a microprocessor, memory 84 for storing instructions for execution by the processor 82, and communications circuitry 86 for communicating between the processor 82 and the patient sensor Examples of suitable processors may include one or more microprocessors, integrated circuits, system-on-a-chips (SoC), among others. Examples of suitable memory, may include one or more primary storage and/or non-primary storage (e.g., secondary, tertiary, etc. storage); permanent, semi-permanent, and/or temporary storage; and/or memory storage devices including but not limited to hard drives (e.g., magnetic, solid state), optical discs (e.g., CD-ROM, DVD-ROM), RAM (e.g., DRAM, SRAM, DRDRAM), ROM (e.g., PROM, EPROM, EEPROM, Flash EEPROM), volatile, and/or non-volatile memory; among others.

In the illustrative embodiment, the patient sensor 12 is connected with the control system 80 by removable wire couple. The control system 80 communicates with the patient sensor 12 for control and/or information. For example, the control system 80 receives signals from the photoelectric detectors 20 indicating light received by each individual detector 20, although in some embodiments, signals from the photoelectric detectors 20 may be combined signals indicating light received collectively by the photoelectric detectors 20. The control system 80 communicates with the patient sensor 12 to govern operation of the light source 36, for example, governing the voltage and/or current provided to the light source 36 to activate and deactivate the light source 36.

In some embodiments, the control system 80 may govern operation of the light source 36 to provide light having variable characteristics to the diffuser 16 and ultimately to the patient. In some embodiments, the patient sensor 12 may be arranged for wireless communication with control system 80, and may include optional wireless communications module 88 comprising processor 90, memory 92 storing instructions for execution by the processor 90, and communications circuitry 94 for sending and receiving signals as directed by the processor 90, for example, to and from the control system 80. In some embodiments, the patient sensor 12 may include an onboard power storage device, such as a battery, for powering wireless communications.

In the illustrative embodiment as shown in FIGS. 2-4, the light diffuser 16 extends radially outward from the axis 15 to distribute light about the canisters 18. The diffuser body 38 is embodied to define a circular disc shape having the diffuser arm 40 extending along the central axis 15 to provide even distribution of light from the light source 36 throughout the diffuser body 38. The diffuser body 38 thus extends radially outward beyond the position of the canisters 18 to envelop the canisters 18 within the light field provided. However, in some embodiments, the radial extent of the diffuser body 38 may be formed with less overlap of the canisters 18, for example, only to extend close to the radially outer edge of the canister wall 60, for example, tangentially with the canister wall 60, or terminating radially between the inner and outer radial extents of each canisters 18.

PPG sensors may include one or more LED's to illuminate the skin, and may include one or more photodetectors (PD's) to measure the changes in infrared light absorption in the blood to determine parameters such as $SpO_2$. Considering wearable sensor devices, the patient's chest can be a site of low perfusion. With the LED and PD's are on the same side of the skin in reflective arrangement, application of sensors to the chest can produce low levels of reflected light at the PD(s) and can present difficulties in light signal detection. Accordingly, there can be advantages to providing chest-worn wearable devices having compact size and performing with high efficiency.

Devices, systems, and methods within the present disclosure may saturate the patient's skin around the sensor with light from the LED to provide a light field. Arranging the PDs within the light field so that the reflected light signals for determining parameters such as $SpO_2$ are directed efficiently into the PDs. Arrangements within the present disclosure include a light pipe/diffuser illuminating the sensor/skin interface. The illuminated sensor face may couple directly to the patient's skin to reduce outside light reflected from the skin surface into the PD's. The light pipe/diffuser is surrounded by a non-transparent (opaque) baffle that supports the optical components and positions the PDs within the reflected light at the sensor/skin interface. The baffle can eliminates the potential for cross-talk from the LED, and from ambient light interference. In some embodiments, the light pipe and baffle can be formed (e.g., molded) as a single component through a second shot and/or insert molding process.

Traditional PPG sensors may arranged lights and PD(s) offset from one another by some spacing. Devices, systems, and methods within the present disclosure may arranged the PDs within the illumination field, improving the sensor's efficiency in terms of light provided and/or received. Arrangements within the present disclosure can eliminate crosstalk (light from the LED directly coupled into the PDs) and ambient light interference, which may represent sources of unwanted "noise."

Illustrative embodiments consider pulse oximetry and PPG sensors specifically for oxygenation detection such as $SpO_2$, but in some embodiments, the devices, systems, and/or methods within the present disclosure may be applied for any suitable physiological parameter, whether directly or indirectly. Illustrative embodiments include arrangement of PPG sensors for reflective light detection, but in some embodiments, PPG sensors may include arrangements for transmissive light detection to determine patient physiological parameters. The illustrative embodiments consider providing and detecting light, embodied as infrared light, for determining patient physiological parameters, but in some embodiments, the light provided and/or received may include any suitable form of light for determining physiological parameters, whether directly or indirectly.

Although certain illustrative embodiments have been described in detail above, variations and modifications exist within the scope and spirit of this disclosure as described and as defined in the following claims.

I claim:

1. A patient sensor, comprising:
   a sensor baffle including a diffuser platform having at least one light opening defined therethrough and at least one canister extending from the diffuser platform to define a light pathway;
   at least one photoelectric detector arranged to receive light through the light pathway of the at least one canister; and
   a light diffuser configured for mounting to the sensor baffle, the light diffuser including a diffuser body and a diffuser arm extending from the body for extension through the at least one light opening to receive light from a light source for diffusion through the diffuser body,
   wherein the diffuser body includes at least one opening arranged to correspond with the at least one canister, the at least one opening configured to receive the at least one canister extending therethrough and at least partly beyond the diffuser body to receive light reflected from a patient's body while blocking against interference light from the diffuser.

2. The patient sensor of claim 1, wherein the diffuser body is configured to disperse light received via the diffuser arm circumferentially about the extension of at least one canister.

3. The patient sensor of claim 1, wherein the diffuser platform includes a first side and the at least one light opening extends between the first side and a second side opposite the first side.

4. The patient sensor of claim 3, wherein the diffuser arm is configured to extend though the light opening to communicate with the light source on the second side of the diffuser platform to receive light for diffusion through the diffuser body.

5. The patient sensor of claim 4, wherein the diffuser arm is flared in shape having decreasing width proceeding away from the diffuser body.

6. The patient sensor of claim 5, wherein the diffuser arm includes a source end formed opposite to the diffuser body that is configured to engage with a light source to receive light for communication through the body.

7. The patient sensor of claim 1, wherein the sensor baffle includes a contact end configured for engagement with a patient's body to allow detection of physiological parameters.

8. The patient sensor of claim 7, wherein the sensor baffle includes a rim extending from the diffuser platform towards the contact end.

9. The patient sensor of claim 8, wherein the rim and the diffuser platform define a diffuser receptacle for receiving the light diffuser.

10. The patient sensor of claim 9, wherein the diffuser receptacle includes an open top for providing diffused light to a patient's body.

11. The patient sensor of claim 10, wherein the at least one canister extends through the diffuser receptacle to receive light reflected from the patient's body through the light pathway.

12. The patient sensor of claim 1, wherein the light pathway of the at least one canister is defined by a tapered inner surface of the at least one canister.

13. The patient sensor of claim 1, wherein the diffuser body includes a backside surface angled away from the diffuser arm.

14. The patient sensor of claim 1, wherein a backside surface of the diffuser body includes texture for directing light through the diffuser body.

15. The patient sensor of claim 14, wherein the texture is arranged annularly about the diffuser arm.

16. The patient sensor of claim 14, wherein the texture is formed with gradient proceeding away from the diffuser arm.

17. The patient sensor of claim 1, wherein the diffuser body includes a frontside surface sloped towards an interior of the diffuser body.

18. The patient sensor of claim 17, wherein the frontside surface is formed to define a depression.

19. The patient sensor of claim 17, wherein the frontside surface is formed to define a negative cone shape.

20. The patient sensor of claim 19, wherein the negative cone shape is tapered.

* * * * *